United States Patent [19]

Nakazawa

[11] 4,072,171
[45] Feb. 7, 1978

[54] PRESSURE CONTROL VALVE FOR A SPHYGMOMANOMETER

[76] Inventor: Shizumasa Nakazawa, 2-10-26, Toneri, Adachi, Tokyo, Japan

[21] Appl. No.: 723,169

[22] Filed: Sept. 14, 1976

[51] Int. Cl.² .............................................. A61B 5/02
[52] U.S. Cl. ............................. 137/599.2; 128/2.05 G
[58] Field of Search ................ 128/2.05 G; 137/599.2

[56] References Cited

U.S. PATENT DOCUMENTS

| 3,254,671 | 6/1966 | Berliner | 128/2.05 G X |
| 3,457,952 | 7/1969 | Smith | 137/599.2 X |

FOREIGN PATENT DOCUMENTS

| 151,601 | 9/1955 | Sweden | 137/599.2 |

Primary Examiner—Robert G. Nilson
Attorney, Agent, or Firm—Haseltine, Lake & Waters

[57] ABSTRACT

A control valve for a sphygmomanometer comprising a valve housing having at one end a communication opening adapted for communication with an arm cuff and at its other end an air supply opening adapted for communication with an elastic bulb for supplying air to the arm cuff. The housing has an air passage connecting the two openings. A tubular body is mounted on the casing to project radially therefrom and the body is connected at its bottom portion through a communication opening to the air passage intermediate the ends thereof. The outer end of the body is open to the atmosphere. A first valve of tubular shape is arranged to open and close an open end of the tubular body and a second valve of rod shape is loosely mounted in an air passage in the first valve and has an outer end projecting externally from the tubular body. The inner end portion of the second valve serves to open and close an open end of the air passage in the first valve. The first valve is restrained in a valve-closing position by a threaded tube screwed on the tubular body and a spring is provided which acts on the first valve in a valve-opening direction and on the second valve in a valve-closing direction. A check valve is mounted on the side of the air supply opening of the valve housing.

7 Claims, 4 Drawing Figures

PRESSURE CONTROL VALVE FOR A SPHYGMOMANOMETER

FIELD OF THE INVENTION

This invention relates to a control valve arrangement in a sphygmomanometer in which during the measuring operation thereof, a fine control of the degree of pressure application by an arm cuff and a rapid release operation of the applied pressure can be carried out easily and conveniently.

SUMMARY OF THE INVENTION

An object of the invention is to provide a control valve for a sphygmomanometer which will satisfy the condition of fine control of the degree of pressure application by the arm cuff and rapid release of the applied pressure.

In accordance with the invention, there is provided a pressure control valve for a sphygmomanometer comprising a housing provided with an air passage having one end adapted for connection to an arm cuff and another end for connection with an air supply, a tubular body secured to said housing and having a hollow interior with a first end communicating with said air passage intermediate the ends thereof and a second open end, first valve means for closing said open end of the tubular body, said first valve means having a bore therein, constituting an air passage having a first end in communication with ambient atmosphere and a second end in communication with the hollow interior of the tubular body, a second valve means loosely and slidably mounted in said bore in said first valve means for selectively opening and closing said second end of the air passage in said first valve means, and external actuator means coupled to said second valve means and slidably actuated to displace the second valve means in said first valve means.

DETAILED DESCRIPTION

Figure 1:
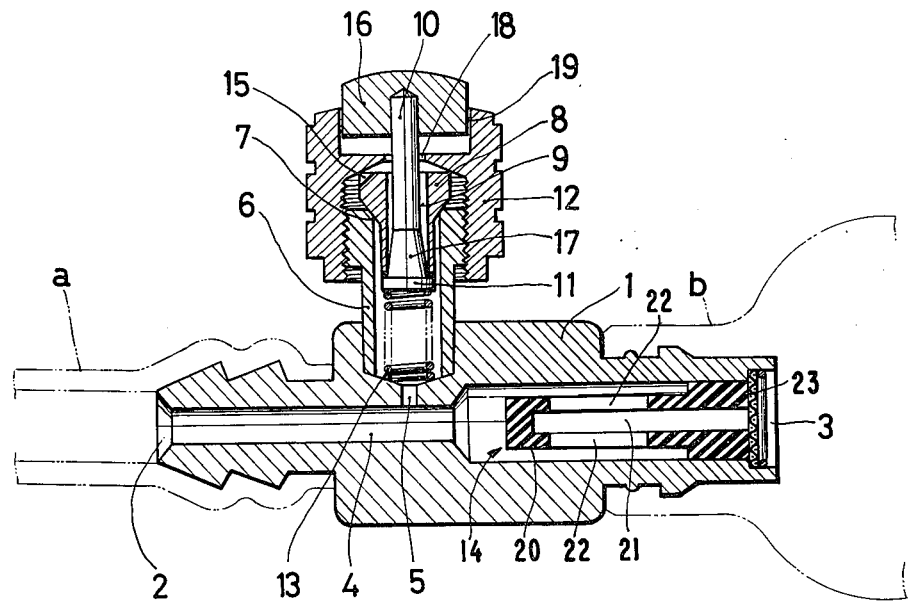
FIG. 1 is a sectional side view of one embodiment according to this invention.
Figure 2:
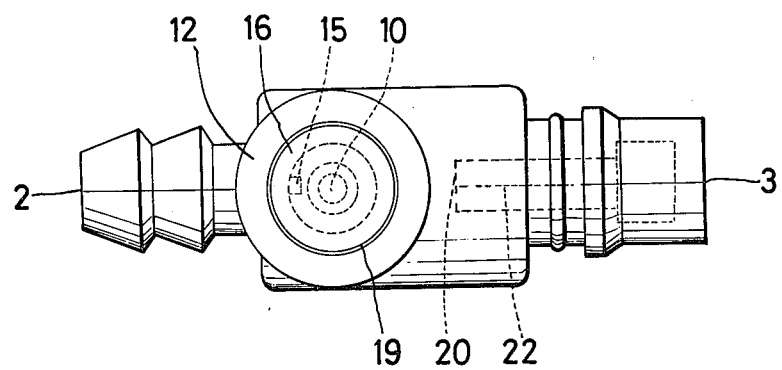
FIG. 2 is a top plan view thereof.

Referring to the drawing, numeral 1 denotes a valve housing which has at one end a communication opening 2 adapted for being connected through a connecting tube *a* to an arm cuff (not shown) and at its other end an air supply opening 3 adapted for being connected to an elastic-bulb *b* for supplying air to the arm cuff. An air passage 4 is provided in the housing 1 establishing communication between the openings 2 and 3.

A tubular body 6 is mounted on the housing 1 and projects radially thereof. The tubular body 6 is in communication at its bottom portion via an opening 5 in housing 1 with an intermediate portion of the air passage 4. A threaded tube 12 is screwed on the tubular body 6 and is movable to advance and retract on body 6. A first valve 8 of tubular form is mounted within tube 12 to come into contact with or be spaced from an outer end 7 of the tubular body 6 for selectively closing and opening the interior of the tubular body 6. An upper edge of the valve 8 is engaged by the threaded tube 12 so that the valve 8 may be brought into pressure contact with the outer end 7 of the tubular body 6 whereby the interior of the tubular body 6 which is in communication with the air passage 4, may be closed off in the closed condition of valve 8. The upper edge of the valve 8 is provided with a cut-out portion 15, so that when the valve 8 is spaced from the outer end 7, the interior of the tubular body 6 is brought into communication with the ambient atmosphere.

Numeral 10 denotes a second valve of rod shape which passes through an air passage 9 in the valve 8 and is loosely inserted in a central opening in the threaded tube 6 such that the outer end portion of valve 10 projects outwardly from tube 12. The valve 10 has an inner end with a larger diameter portion 11 thereat such that the open end of the air passage 9 may be closed and opened by causing the portion 11 to come selectively into contact with or be spaced apart from the lower end of the first valve 8. The second valve 10 is acted on by a spring 13 contained in the tubular body 6 so that the valve 10 is normally urged to close the open end of the air passage 9, the force of spring 13 also acting through the second valve 10 on the first valve 8 in such a direction that the first valve 8 tends to be spaced from the outer open end 7 of the tubular body 6, that is, in an opened position.

A pushing operation member 16 is integrally secured to the outer projecting end of valve 10. A base portion of the second valve 10 extending to the larger diameter portion 11 of valve 10 is formed as a taper portion 17 gradually increasing in diameter towards the inner end of the valve such that when the second valve 10 is pushed inwardly against the action of the spring 13 by pushing the operation member 16 whereby the open end of the air passage 9 is opened, the degree of opening of the air passage 9 gradually increases in proportion to the displacement of valve 10 and thereby the amount of air which is passed is increased accordingly. Additionally, when the first valve 8 and the second valve 10 are opened, the inner bore of the tubular body 6 and the interior of the air passage 9 of the first valve 8 are in communication with the ambient atmosphere through the cut-out portion 15, an opening 18 in the threaded tube 12 through which the second valve 10 passes and a gap 19 formed between the operation member 16 and the threaded tube 12.

Numeral 14 denotes a check valve which is mounted in the air passage 4 at the side thereof proximate opening 3 and the check valve is of the type by which the passage 4 is opened only when air is supplied to the arm cuff by squeezing the elastic bulb *b*. In the illustrated embodiment, the check valve comprises a tubular body 20 made of elastic material, such as rubber or the like, having a blind bore 21 extending in the air supply direction. The body 20 has a larger diameter portion tightly mounted in the air supply passage 4. The body 20 has radial cuts 22 in its tubular portion communicating with the bore 21 such that at the time of air supply, the cuts 22 are opened by the supply air pressure to allow the air to pass therethrough, whereas under pressure in the reverse direction, the edges of the body 20 bordering the cuts 22 are brought into tightly sealed contact so that reverse travel of the air is prevented.

Numeral 23 denotes a dust-proof wire mesh plate mounted in the air supply opening 3.

In the device according to the invention, the arm cuff is supplied with air through the air passage 4 by compression of the elastic bulb *b* and the cuff is expanded to compress the upper arm of the patent, until the patient's pulses no longer can be heard. During the time of this air supply, the first valve 8 and the second valve 10 remain in their closed conditions as shown in FIG. 1, so that the supplied air is sent into the cuff without any leakage and thereby the upper arm of the patient is compressed smoothly and rapidly by the expansion of the cuff.

Figure 3:
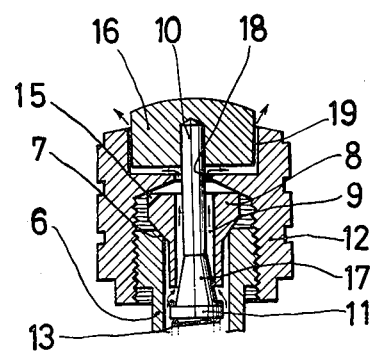
FIG. 3 is a sectional side view of a portion thereof at the time of air leakage operation.
Figure 4:
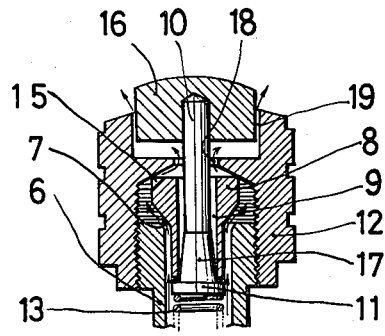
FIG. 4 is a sectional side view of the same portion at the time of rapid release of accumulated pressure.

In order to hear the pulses for measuring the blood pressure, the pressure applied by the supply of air is released by depressing the operation member 16 against the action of the spring 13 as shown in FIG. 3. Thereby, the larger diameter portion 11 of the second valve 10 is spaced from the open end of the air passage 9, so that the pressure air is gradually leaked out to the atmosphere through the air passage 4, the communication opening 5 and the air passage 9. Since the base portion of the second valve 10 is formed with the taper portion 17 as illustrated, the rate of air leakage is increased in accordance with the degree of displacement of the second valve 10 by the operation member 16.

Thus, the pressure at the time when the pulses begin to be heard in the course of the air leakage is measured by a measuring device connected to the cuff and indicates the systolic pressure of the maximum value of the blood pressure, whereas upon successive air leakage by continued operation of the second valve 10, the last sound of the disappearing pulse is detected and the pressure at that time is measured as the diastolic pressure or the minimum value of the blood pressure by the measuring device. At each time of measuring of the maximum value and the minimum value of the blood pressure, it is necessary for the measuring to be accurate and the air leakage speed is decreased so that the movement of a pointer or a column of the measuring device is made slow, so that a precise manual control becomes necessary for pushing of the operation member 16.

If, after completion of the measuring, the threaded tube 12 is screwed backwards, the first valve 8 is released from the pressure of the threaded tube 12 and the valve 8 is pushed outwards by the action of the spring 13 acting on the second valve 10 and thus is spaced from the open outer end 7 of the tubular body 6 to open the same, whereby the accumulated air is leaked out rapidly and the pointer or the column is returned to its zero position. From this condition, the threaded tube 12 is again screwed in and the first valve 8 is brought to its valve closing condition for being ready for the next measuring operation.

Thus, according to this invention, the air leakage is effected by valve-opening by pushing-in of the second valve 10 at the time of measuring, so that a fine control by manual operation can be obtained exteremly easily and accurately as compared with the conventional case wherein this is effected by a turning operation of an adjusting ring or the like, whereas release of the accumulated pressure is effected rapidly by opening of the first valve 8 by turning of the threaded tube 12, so that the handling and operation thereof by an operator is extremely easy and accordingly an accurate measurement can be effected.

What is claimed is:

1. A pressure control valve for a sphygmomanometer comprising a housing provided with an air passage having one end adapted for connection to an arm cuff and another end for connection with an air supply, a tubular body secured to said housing and having a hollow interior with a first end communicating with said air passage intermediate the ends thereof and a second open end, first valve means for closing said open end of the tubular body, said first valve means having a bore therein constituting an air passage having a first end in communication with ambient atmosphere and a second end in communication with the hollow interior of the tubular body, a second valve means loosely and slidably mounted in said bore in said first valve means for selectively opening and closing said second end of the air passage in said first valve means, external actuator means coupled to said second valve means and slidably actuated to displace the second valve means in said first valve means, spring means acting on said second valve means for closing said second end of the air passage in said first valve means, and a threaded member screwed on said tubular body for engaging said first valve means to hold the same in closed position against the open end of the tubular body, said second valve means including a portion bearing against said first valve means in the closed position of said second end of the air passage in said first valve means, said spring means acting on said first valve means through said portion on said second valve means to urge the first valve means in a direction tending to open said second end of the tubular body.

2. A pressure control valve as claimed in claim 1 wherein said second valve means includes a tapered portion which passes through said second end of said air passage in said first valve means as said second valve means is displaced in said first valve means, said tapered portion having gradually reduced section to provide successively increasing clearance space with said second end as said second valve means is progressively displaced in said first valve means from said closed position of the second end of the air passage in said first valve means.

3. A pressure control valve as claimed in claim 2 wherein said second valve means further includes a rod portion extending loosely in said bore of said first valve means and projecting externally of said threaded member in connection with said external actuator means, said rod being connected to said tapered portion.

4. A pressure control valve as claimed in claim 3 wherein said threaded member has a recess slidably accommodating said external actuator means with clearance.

5. A pressure control valve as claimed in claim 3 wherein said external actuator means is secured to said rod, said portion of the second valve means which bears against said first valve means in the closed position of the second end of the air passage of the first valve means being of larger section than the largest section of said tapered portion.

6. A pressure control valve as claimed in claim 3 wherein said first valve means has an end bearing against said threaded member which end is provided with a cut-out portion.

7. A pressure control valve as claimed in claim 1 comprising check valve means for admitting air from said air supply into said air passage while preventing reverse flow from the air passage to said air supply.

* * * * *